United States Patent [19]

Newman et al.

[11] Patent Number: 5,011,778
[45] Date of Patent: Apr. 30, 1991

[54] MONOCLONAL ANTIBODIES DIRECTED TO IL-1 ACTIVATED ENDOTHELIAL CELLS AND MEDICAMENTS EMPLOYING THE MONOCLONAL ANTIBODIES

[75] Inventors: Walter Newman; Diane O. Wilson, both of Rockville, Md.

[73] Assignee: Otsuka Pharmaceutical Co., Ltd., Rockville, Md.

[21] Appl. No.: 355,701

[22] Filed: May 23, 1989

[51] Int. Cl.$^5$ .................. C12N 5/20; C07K 15/28; A61K 39/00

[52] U.S. Cl. ............... 435/240.27; 530/387; 424/85.8; 435/70.21; 435/172.2

[58] Field of Search ............ 435/240.27, 70.21, 172.2; 530/387; 424/85.8; 935/104

[56] References Cited

PUBLICATIONS

Osborn, Cell, 62:3–6, 1990.
Smith et al., J. Clin. Invest., 82:1746, 1988.
Bevilacqua et al., Identification of an Inducible Endothelial–Leukocyte Adhesion Molecule, PNAS, 84:9238–9244, 1987.
Rothlein et al., A Humanintercellular Adhesion Molecule (ICAM-1) Distinct from LFA-1, J. Immunology, 137:1270–74, 1986.
Bevilacqua, M. P., et al., Science, 243:1160–1165, (Mar. 3, 1989).
Pober, J. S., et al., The Journal of Immunology, 136:5, pp. 1680–1684, (Mar. 1, 1986).
Bevilacqua, M. P., et al., Proc. Natl. Acad. Sci. U.S.A., 84:9238–9242, (Dec. 1987).
McEver, R. P., et al., The Journal of Biological Chemistry, 259:15, 9799–9804, (Aug. 10, 1984).
Hsu-Lin, Shu-Chu, et al., The Journal of Biological Chemistry, 259:14, 9121–9216, (Jul. 25, 1984).
Goerdt, Sergij, et al., Expl. Cell Biol., 55:117–126, (1987).
Stoolman, Lloyd M., Cell: 56, 907–910, (Mar. 24, 1989).
Staunton, Donald E., et al., Cell: 52, 925–933, (Mar. 25, 1988).

Primary Examiner—Esther L. Kepplinger
Assistant Examiner—Paula Hutzell
Attorney, Agent, or Firm—Sughrue, Mion, Zinn, Macpeak & Seas

[57] ABSTRACT

Hybridoma cell lines are made that produce monoclonal antibodies having, among others, the following identifying characteristics: (1) bind to IL-1 activated endothelial cells; (2) do not bind significantly to normal resting endothelial cells; (3) do not bind significantly to normal resting or IL-1 activated epidermal keratinocytes or resting or IL-1 activated fibroblasts. The monoclonal antibodies are used in therapeutic compositions for blocking inflammatory responses associated with activated endothelial cells.

6 Claims, 6 Drawing Sheets

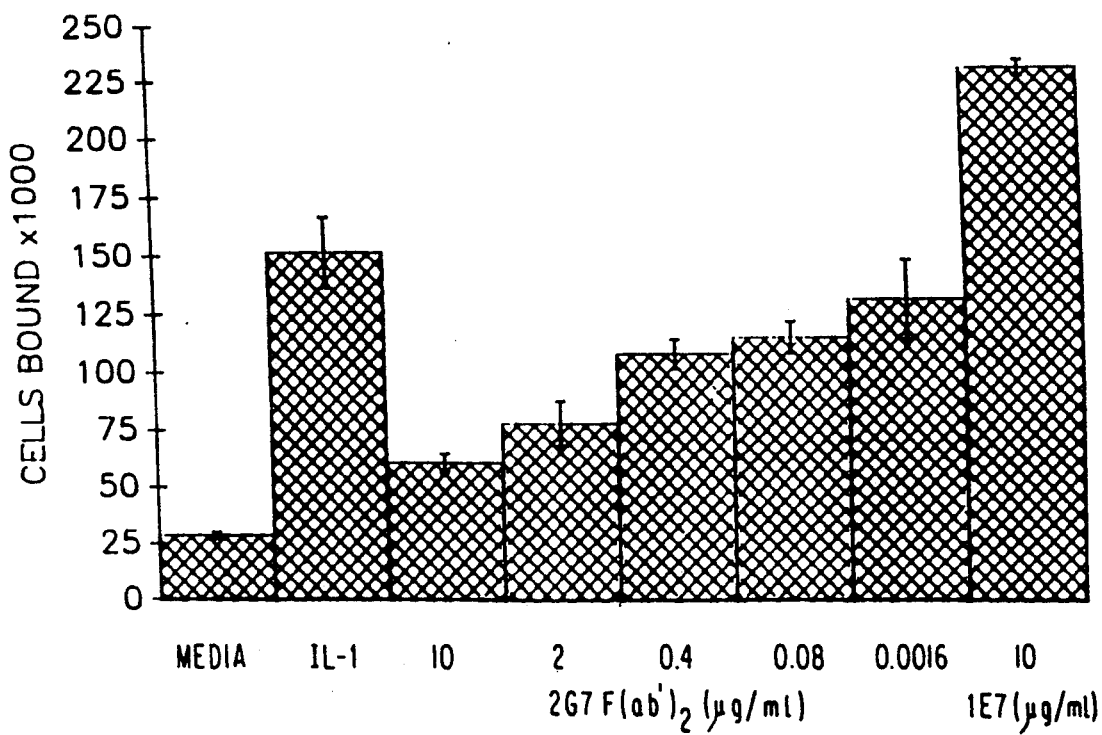
FIG.2 INHIBITION OF MONONUCLEAR CELL BINDING TO IL-1 ACTIVATED HUVECS

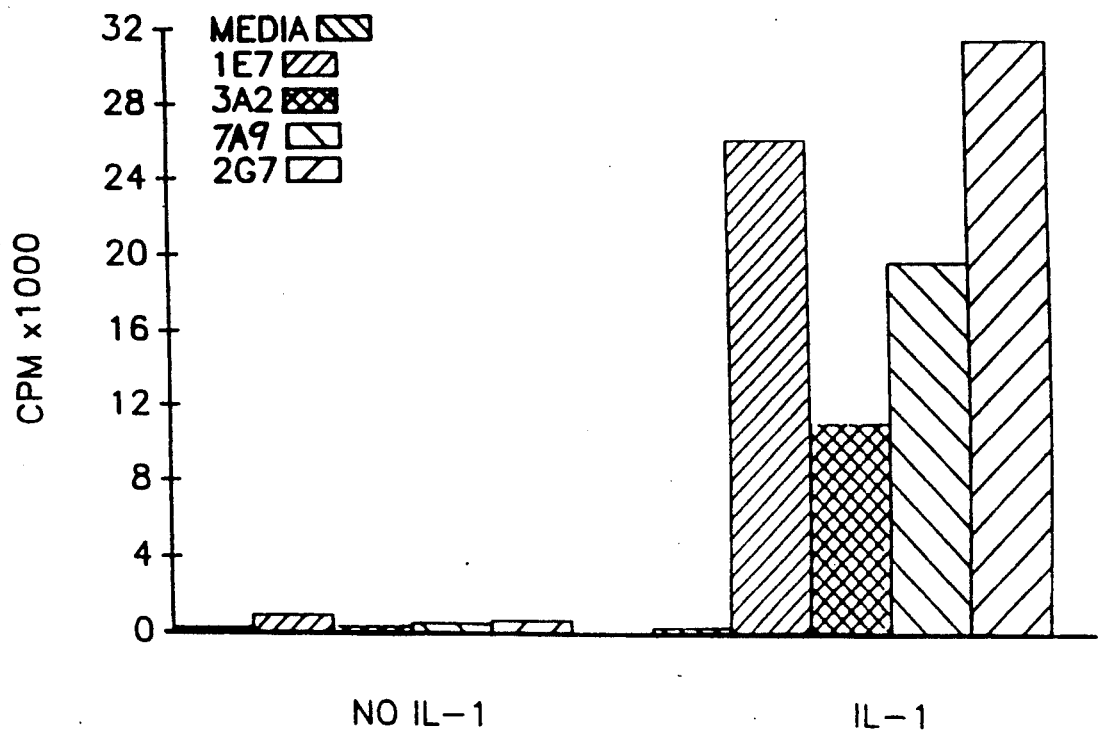
FIG. 5 EFFECT OF IL-1 ON EC ANTIGEN EXPRESSION.
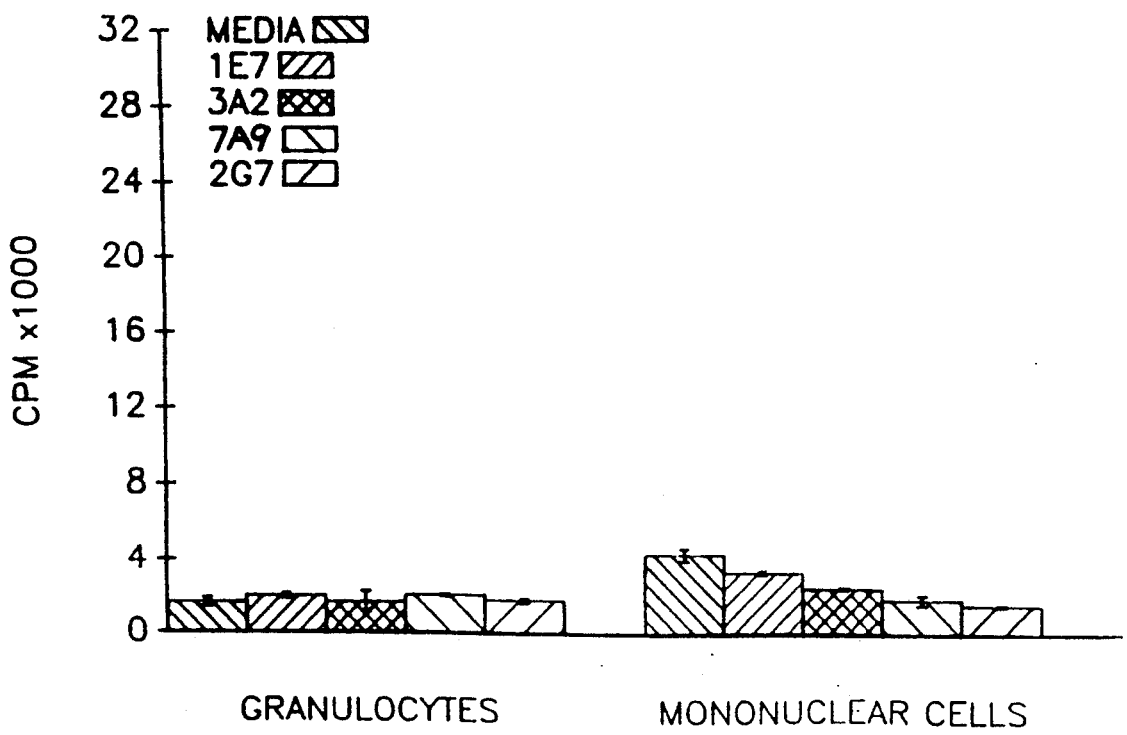
FIG. 6 ENDOTHELIAL ANTIGEN EXPRESSION ON LEUCOCYTES.

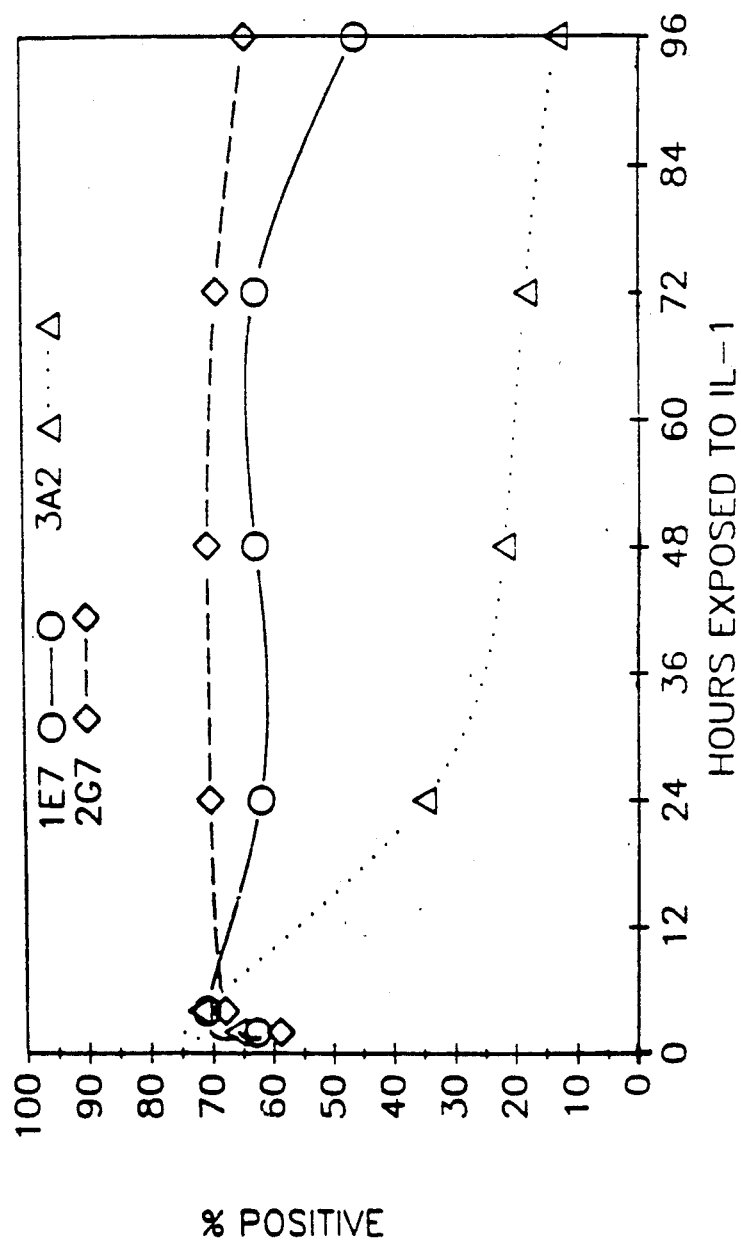

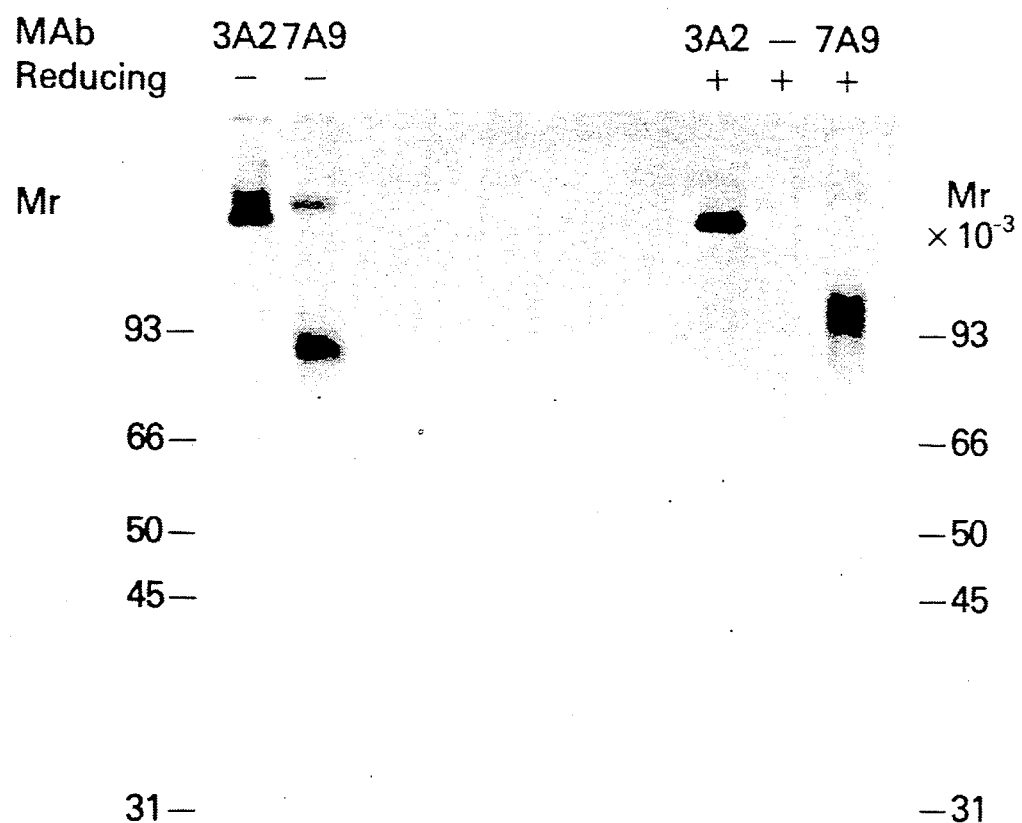

MONOCLONAL ANTIBODIES DIRECTED TO IL-1 ACTIVATED ENDOTHELIAL CELLS AND MEDICAMENTS EMPLOYING THE MONOCLONAL ANTIBODIES

FIELD OF THE INVENTION

The present invention relates to monoclonal antibodies and their applications to inflammatory processes. More particularly, the present invention relates to new monoclonal antibodies that are directed to activated endothelial cells in vitro and in vivo. The present invention also relates to new endothelial cell surface antigens which are induced as a consequence of IL-1 treatment. Some of the new monoclonal antibodies as well as the new antigens are useful as medicaments for treating both acute and chronic inflammatory responses associated with endothelial cells and the present invention further relates to such medicaments as well as to methods for treating such inflammatory responses. Additionally, the present invention relates to methods of detecting inflammatory responses associated with endothelial cells such as early graft rejection, subclinical infection, and vasculitis.

BACKGROUND OF THE INVENTION

Endothelial cells (EC) are major participants in chronic and acute inflammation. They regulate the passage of cells and fluids between the bloodstream and the extravascular space. In addition, they respond to inflammatory stimuli by secreting factors which have a variety of effects on hematopoiesis (Quesenberry and Gimbrone, *Blood.* 56: 1060–1067, 1980), chemotaxis (Streiter et al, *Science,* 243: 1467–1469, 1989), and coagulation (Bevilacqua et al, *J. Exp. Med.,* 160: 618–623, 1984). Interleukin 1 (IL-1) is secreted by a wide range of cell types as an almost universal response of cells to injury (Neta and Oppenheim, *Ann. Int. Med.* 109: 1–31, 1988). Many cell types secrete this factor under appropriate stimulation, and many cell types respond, and in a variety of ways. IL-1 is found at sites of inflammation, and when injected as a purified protein, results in erythema and an influx of granulocytes from the bloodstream and secondarily, tissue destruction (Beck et al, *J. Immunol.,* 136: 3025–3031, 1986: Pettipher et al. *Proc. Nat'l. Acad. Sci.,* 83: 8749–8753, 1986).

Several laboratories have shown that endothelial cells have a rapid response to IL-1 which is consistent with their accessory nature in the inflammatory reaction. Two of the best described responses are an increase in procoagulant activity (Bevilacqua et al. 1984, supra) and a concomitant increase in adhesive capacity for leucocytes (Bevilacqua et al. *J. Clin. Invest.,* 76: 2003–2011, 1985).

As the lining of blood vessels, endothelial cells are uniquely positioned to regulate the traffic in inflammatory cells and their reactive by-products. In addition, endothelial cells can themselves secrete into the bloodstream newly synthesized proteins which may be an early indicator of the inflammatory process. Despite this key role, very few therapeutic approaches or diagnostic indicators have been developed that directly address the role of this cell type. The biology of endothelial cells is starting to be understood now in much better detail due to the recent success in culturing these cells in the laboratory.

As mentioned above, a key mediator of the inflammatory response is IL-1. IL-1 is a 17 Kd polypeptide secreted by macrophages and many other cell types which is capable of eliciting a wide array of responses ranging from induction of fever, to proliferation of inflammatory cells and the recruitment of mature leucocytes from precursors in the bone marrow (reviewed by Dinarello, *FASEB J.,* 2: 106–115, 1988).

Endothelial cells both respond to and secrete IL-1 at a very early stage of the inflammatory process. While a byproduct of bacterial infection with gram negative organisms is the production of endotoxin and the consequent secondary production of IL-1, the issue of whether mechanical injury can trigger IL-1 release is a critical but as yet unanswered question for students of sports-induced inflammation.

It is believed, based upon work by several laboratories in the past decade, that the binding of leucocytes to the vascular wall, a process that can be mimicked in vitro with IL-1 treatment of endothelial cells, is the first step in the diapedesis of leucocytes into the tissue space. However, several aspects of this process, especially as they may be related to the utility of current anti-inflammatory agents for intervention, remain unclear.

IL-1 induces a rapid alteration in the membrane properties of cultured human endothelial cells. This is evident from the ability of treated cells to bind leucocytes, their acquisition of procoagulant activity and the expression of new cell surface antigens including some for which no functional property has yet been assigned. In those cases studied, the development of the new properties described is sensitive to the action of actinomycin D and cycloheximide, suggesting a requirement for the synthesis of new message and new proteins.

Binding of leucocytes to basal and activated endothelial cells has been studied by several laboratories. Evidence has been presented that granulocytes, monocytes T-, B- and NK cells all can bind to endothelial cells after stimulation with very low concentrations of IL-1, on the order of $10^{-10}$M. The suggestion has been made that more than 1 endothelial cell membrane protein is involved in the adhesion process. Two laboratories have presented evidence in the case of granulocytes that the 90 Kd protein termed intercellular adhesion molecule (ICAM) as well as the 115 Kd molecule termed endothelial leucocyte adhesion molecule (ELAM) contribute to cytokine induced adhesion. Nonetheless, the role of these and other molecules in the binding of mononuclear cells remains to be clarified.

SUMMARY OF THE INVENTION

Accordingly, one object of the present invention is to develop new monoclonal antibodies that are specific to antigens on activated human endothelial cells, both in vitro and in vivo.

A second object of the present invention is to develop new monoclonal antibodies that block binding of white blood cells, thereby making the monoclonal antibodies useful as medicaments and in methods for intervening in inflammatory responses associated with activated endothelial cells.

A third object of the present invention is to provide a new antigen exhibited on activated endothelial cells which is useful as a medicament and in a method for intervening in inflammatory responses associated with activated endothelial cells.

A fourth object of the present invention is to provide a detection method capable of detecting inflammatory responses associated with activated endothelial cells.

These and other objects have been achieved by providing a hybridoma that produces a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells, B-cells and monocytes);
(5) does not block binding of a mixture of mononuclear cells comprising T-cells, B-cells and NK cells to IL-1 activated endothelial cells in vitro;
(6) distribution of antigen: IL-1 activated endothelial cells;
(7) antigen size, as measured by SDS polyacrylamide gel electrophoresis under reducing conditions:
(a) major band at about 125 Kd,
(b) minor band at about 97 Kd;
(8) antigen size, as measured by SDS polyacrylamide gel electrophoresis under non-reducing conditions:
(a) major band at about 99 Kd,
(b) minor band at about 87 Kd; and
(9) exhibits chronic kinetics as determined by ability of the monoclonal antibody to bind to endothelial cells pretreated for increasingly longer periods of time with IL-1.

The present invention also provides a hybridoma that produces a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocyte or mononuclear cells (T-cells, and B-cells and monocytes);
(5) partially blocks binding of a mixture of cells comprising T-cells B-cells and monocytes to IL-1 activated endothelial cells in vitro;
(6) distribution of antigen: IL-1 activated endothelial cells;
(7) antigen size, as measured by SDS polyacrylamide gel electrophoresis under reducing conditions:
(1) major band at about 125 Kd,
(b) minor band at about 97 Kd;
(8) antigen size, as measured by SDS polyacrylamide gel electrophoresis under non-reducing conditions:
(a) major band at about 99 Kd,
(b) minor band at about 87 Kd; and
(9) antigen exhibits chronic kinetics as determined by ability of the monoclonal antibody to bind to endothelial cells pretreated for increasingly longer periods of time with IL-1.

The present invention also provides a hybridoma that produces a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated human granulocytes or mononuclear cells (T-cells, B-cells and monocytes);
(5) distribution of antigen: IL-1 activated endothelial cells;
(6) antigen size, as measured by SDS polyacrylamide gel electrophoresis under reducing and non-reducing conditions: 177 Kd; and
(7) antigen exhibits acute kinetics as determined by ability of the monoclonal antibody to bind to human endothelial cells pretreated for increasingly longer periods of time with IL-1.

The present invention also provides a hybridoma that produces a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells, B-cells and monocytes);
(5) blocks binding of granulocytes to IL-1 activated endothelial cells in vitro;
(6) partially blocks binding of monocytes to IL-1 activated endothelial cells in vitro;
(7) distribution of antigen: IL-1 activated endothelial cells;
(8) antigen size, as measured by SDS polyacrylamide gel electrophoresis under reducing conditions: about 100 Kd; and
(9) antigen size, as measured by SDS polyacrylamide gel electrophoresis under non-reducing conditions: about 90 Kd.

In a further embodiment, the present invention provides the above-described monoclonal antibodies.

In preferred embodiments, the monoclonal antibodies are monoclonal antibody 1E7, produced by hybridoma cell line 1E7 having ATCC Deposit No. HB 10136, monoclonal antibody 2G7 produced by hybridoma 2G7 having ATCC Deposit No. HB 10137, monoclonal antibody 3A2 produced by hybridoma 3A2 having ATCC Deposit No. HB 10138, and monoclonal antibody 7A9 having ATCC Deposit No. HB 10135.

In an even further embodiment, the present invention provides a medicament for blocking inflammatory responses associated with activated endothelial cells the medicament comprising:
(A) a pharmaceutically effective amount of an antibody binding site of a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells. B-cells and monocytes);
(5) partially blocks binding of a mixture of cells comprising T-cells, B-cells and monocytes to IL-1 activated endothelial cells in vitro;
(6) distribution of antigen: IL-1 activated endothelial cells;

(7) antigen size, as measured by SDS polyacrylamide gel electrophoresis under reducing conditions:
  (a) major band at about 125 Kd,
  (b) minor band at about 97 Kd;
(8) antigen size, as measured by SDS polyacrylamide gel electrophoresis under non-reducing conditions:
  (a) major band at about 99 Kd,
  (b) minor band at about 87 Kd; and
(9) antigen exhibits chronic kinetics as determined by ability of the monoclonal antibody to bind to endothelial cells pretreated for increasingly longer periods of time with IL-1; and
(B) a pharmaceutically acceptable carrier, diluent or excipient.

The invention also provides a medicament for blocking inflammatory responses associated with activated endothelial cells, the medicament comprising:
(A) a pharmaceutically effective amount of an antibody binding site of a monoclonal antibody having the following identifying characteristics:
  (1) binds to IL-1 activated endothelial cells;
  (2) does not bind significantly to normal resting endothelial cells;
  (3) does not bind significantly to normal resting or IL-1 activated epidermal keratinocytes or resting or IL-1 activated fibroblasts;
  (4) does not bind significantly to normal resting or IL-1 activated granulocytes or mononuclear cells (T-cells. B-cells and monocytes);
  (5) blocks binding of granulocytes to IL-1 activated endothelial cells in vitro;
  (6) partially blocks binding of monocytes to IL-1 activated endothelial cells in vitro:
  (7) distribution of antigen: IL-1 activated endothelial cells;
  (8) antigen size, as measured by SDS polyacrylamide gel electrophoresis under reducing conditions: about 100 Kd; and
  (9) antigen size, as measured by SDS polyacrylamide gel electrophoresis under non-reducing conditions: about 90 Kd.
(B) a pharmaceutically acceptable carrier, diluent or excipient.

In a preferred embodiment, the monoclonal antibodies are monoclonal antibody 2G7 produced by hybridoma cell line 2G7 having ATCC Deposit No. HB 10137, and monoclonal antibody 7A9 produced by hybridoma cell line 7A9 having ATCC Deposit No. HB 10135.

In still another embodiment, the present invention provides a method for blocking inflammatory responses associated with activated endothelial cells, the method comprising treating a subject in need of treatment with a pharmaceutically effective amount of an antibody binding site of a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells, B-cells and monocytes):
(5) partially blocks binding of a mixture of cells comprising T-cells. B-cells and monocytes to IL-1 activated endothelial cells in vitro:
(6) distribution of antigen: IL-1 activated endothelial cells:
(7) antigen size, as measured by SDS polyacrylamide gel electrophoresis under reducing conditions:
  (a) major band at about 125 Kd,
  (b) minor band at about 97 Kd;
(8) antigen size, as measured by SDS polyacrylamide gel electrophoresis under non-reducing conditions:
  (a) major band at about 99 Kd,
  (b) minor band at about 87 Kd; and
(9) antigen exhibits chronic kinetics as determined by ability of the monoclonal antibody to bind to endothelial cells pretreated for increasingly longer periods of time with IL-1.

The present invention also provides a method for blocking inflammatory responses associated with activated endothelial cells, the method comprising treating a subject in need of treatment with a pharmaceutically effective amount of an antibody binding site of a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells, B-cells and monocytes);
(5) blocks binding of granulocytes to IL-1 activated endothelial cells in vitro;
(6) partially blocks binding of monocytes to IL-1 activated endothelial cells in vitro;
(7) distribution of antigen: IL-1 activated endothelial cells;
(8) antigen size, as measured by SDS polyacrylamide gel electrophoresis under reducing conditions: about 100 Kd; and
(9) antigen size, as measured by SDS polyacrylamide gel electrophoresis under non-reducing conditions: about 90 Kd.

In a preferred embodiment the monoclonal antibodies are monoclonal antibody 2G7 produced by hybridoma cell line 2G7 having ATCC Deposit No. HB 10137, and monoclonal antibody 7A9 produced by hybridoma cell line 7A9 having ATCC Deposit No. HB 10135.

The present invention further provides:

A purified antigen or antigenic fragment thereof, the antigen having the following identifying characteristics:
(1) distribution: IL-1 activated human endothelial cells;
(2) size as measured by SDS polyacrylamide gel electrophoresis under reducing conditions: about 100 Kd;
(3) size as measured by SDS polyacrylamide gel electrophoresis under non-reducing conditions: about 90 Kd; and
(4) binds to monoclonal antibody 7A9 produced by hybridoma cell line 7A9 having ATCC Deposit No. HB 10135;

A medicament for blocking inflammatory responses associated with activated endothelial cells, the medicament comprising:

(A) a pharmaceutically effective amount of a purified antigen or antigenic fragment thereof, the antigen having the following identifying characteristics:
  (1) distribution: IL-1 activated human endothelial cells;
  (2) size as measured by SDS polyacrylamide gel electrophoresis under reducing conditions: about 100 Kd;
  (3) size as measured by SDS polyacrylamide gel electrophoresis under non-reducing conditions: about 90 Kd; and
  (4) binds to monoclonal antibody 7A9 produced by hybridoma cell line 7A9 having ATCC Deposit No. HB 10135; and
(B) a pharmaceutically acceptable carrier, diluent or excipient; and A method for blocking inflammatory responses associated with activated endothelial cells, the method comprising treating a subject in need of treatment with a pharmaceutically effective amount of a purified antigen or antigenic fragment thereof, the purified antigen having the following identifying characteristics:
  (1) distribution: IL-1 activated human endothelial cells;
  (2) size as measured by SDS polyacrylamide gel electrophoresis under reducing conditions: about 100 Kd;
  (3) size as measured by SDS polyacrylamide gel electrophoresis under non-reducing conditions: about 90 Kd; and
  (4) binds to monoclonal antibody 7A9 produced by hybridoma cell line 7A9 having ATCC Deposit No. HB 10135.

Finally, the present invention provides a method for detecting inflammatory responses associated with activated endothelial cells, the method comprising:
(I) contacting a test sample with an antibody selected from the group consisting of:
  (A) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells, B-cells, and monocytes);
    (5) does not block binding of a mixture of mononuclear cells comprising T-cells, B-cells and NK cells to IL-1 activated endothelial cells in vitro;
    (6) distribution of antigen: IL1 activated endothelial cells;
    (7) antigen size, as measured by SDS polyacrylamide gel electrophoresis under reducing conditions:
      (a) major band at about 125 Kd,
      (b) minor band at about 97 Kd;
    (8) antigen size, as measured by SDS polyacrylamide gel electrophoresis under non-reducing conditions:
      (a) major band at about 99 Kd,
      (b) minor band at about 87 Kd; and
    (9) exhibits chronic kinetics as determined by ability of the monoclonal antibody to bind to endothelial cells pretreated for increasingly longer periods of time with IL-1;
  (B) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells, B-cells and monocytes);
    (5) partially blocks binding of a mixture of cells comprising T-cells B-cells and monocytes to IL-1 active endothelial cells in vitro;
    (6) distribution of antigen: IL-1 activated endothelial cells;
    (7) antigen size, as measured by SDS polyacrylamide gel electrophoresis under reducing conditions:
      (a) major band at about 125 Kd,
      (b) minor band at about 97 Kd;
    (8) antigen size, as measured by SDS polyacrylamide gel electrophoresis under non-reducing conditions:
      (a) major band at about 99 Kd,
      (b) minor band at about 87 Kd: and
    (9) antigen exhibits chronic kinetics as determined by ability of monoclonal antibody to bind to endothelial cells pretreated for increasingly longer periods of time with IL-1;
  (C) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells, B-cells and monocytes);
    (5) distribution of antigen: IL-1 activated endothelial cells;
    (6) antigen size, as measured by SDS polyacrylamide gel electrophoresis under reducing and non-reducing conditions: about 177 Kd; and
    (7) antigen exhibits acute kinetics as determined by ability of the monoclonal antibody to bind to endothelial cells pretreated for increasingly longer periods of time with IL-1; and
  (D) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells B-cells and monocytes);
    (5) blocks binding of granulocytes to IL-1 activated endothelial cells in vitro;
    (6) partially blocks binding of monocytes to IL-1 activated endothelial cells in vitro;

(7) distribution of antigen: IL-1 activated endothelial cells;
(8) antigen size as measured by SDS polyacrylamide gel electrophoresis under reducing conditions: about 100 Kd; and
(9) antigen size, as measured by SDS polyacrylamide gel electrophoresis under non-reducing conditions: about 90 Kd; and (II) assaying for specific binding of said antibody to antigen in said test sample.

The present invention also provides a method for detecting inflammatory responses associated with activated endothelial cells, the method comprising:
(I) contacting a blood sample with an antibody selected from the group consisting of:
  (A) a monoclonal having the identifying characteristics of monoclonal antibody 1E7 produced by hybridoma 1E7 having ATCC Deposit No. HB 10136;
  (B) a monoclonal having the identifying characteristics of monoclonal antibody 2G7 produced by hybridoma 2G7 having ATCC Deposit No. HB 10137;
  (C) a monoclonal having the identifying characteristics of monoclonal antibody 3A2 produced by hybridoma 3A2 having ATCC Deposit No. HB 10138;
  (D) a monoclonal having the identifying characteristics of monoclonal antibody 7A9 produced by hybridoma 7A9 having ATCC Deposit No. HB 10135.

In a preferred embodiment, the monoclonal antibodies are monoclonal antibody 1E7, produced by hybridoma cell line 1E7 having ATCC Deposit No. HB 10136, monoclonal antibody 2G7 produced by hybridoma cell line 2G7 having ATCC Deposit No. HB 10137, monoclonal antibody 3A2, produced by hybridoma cell line 3A2 having ATCC Deposit No. HB and monoclonal antibody 7A9, produced by hybridoma cell line 7A9 having ATCC Deposit No. HB 10135.

BRIEF DESCRIPTION OF THE FIGURES

FIG. 2 is a graph showing inhibition of the binding of human mononuclear cells to IL-1 activated endothelial cells pretreated with the F(ab')$_2$ fragment of monoclonal antibody 2G7 or with monoclonal antibody 1E7 of the present invention.

FIG. 4 is an SDS-PAGE pattern (8% acrylamide) of the antigens defined by the monoclonal antibodies 3A2 and 7A9 of the present invention under reducing and non-reducing conditions. Molecular weight standards are also shown.

FIG. 5 is a graph showing binding of the monoclonal antibodies according to the present invention to normal resting and IL-1 activated endothelial cells (EC).

FIG. 6 is a graph showing binding of the monoclonal antibodies according to the present invention to normal human white blood cells, either granulocytes or mononuclear cells (T-cells, B-cells, and monocytes) in either the presence or absence of IL-1.

FIG. 7 is a graph showing binding of the monoclonal antibodies according to the present invention to endothelial cells exposed to IL-1 for varying time periods from 2 hours to 96 hours.

DETAILED DESCRIPTION OF THE INVENTION

Hybridomas and Monoclonal Antibodies

Figure 1:
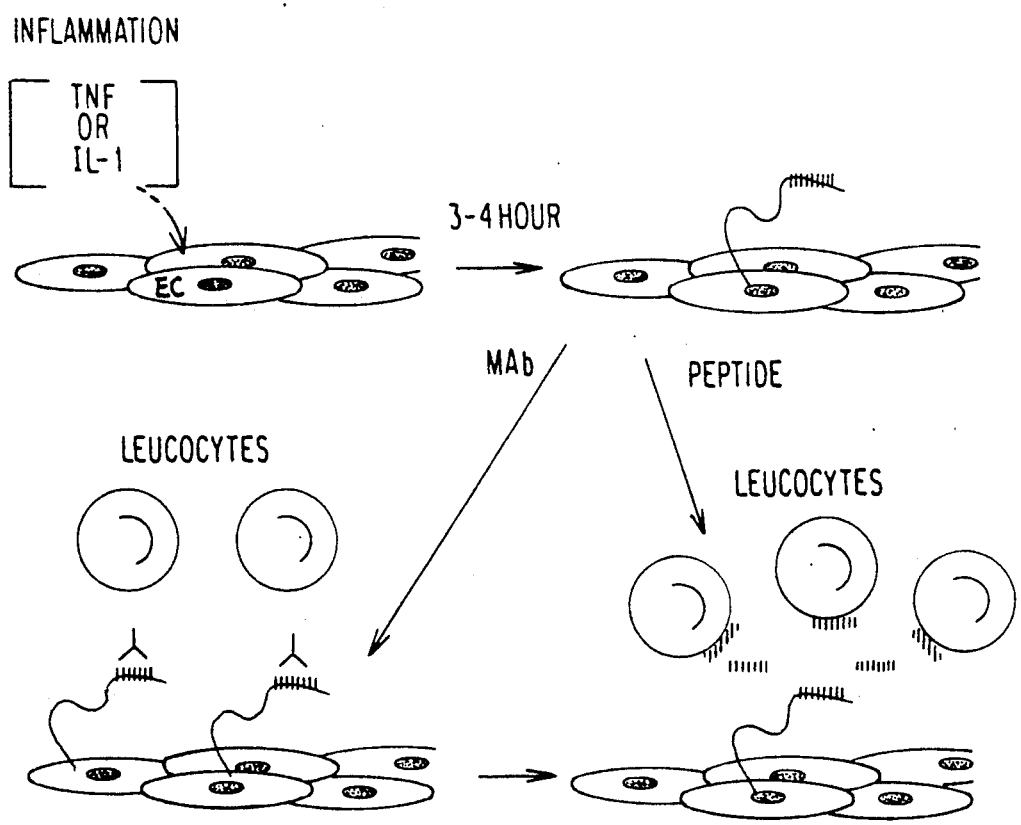
FIG. 1 is a schematic representation of the mechanism by which the novel monoclonal antibodies (MAb) of the present invention that block binding of white blood cells to IL-1 activated endothelial cells and by which the novel antigen (Peptide) according to the present invention act to block inflammation.

The present invention provides novel hybridomas that produce novel murine monoclonal antibodies having identifying characteristics described above and in the Examples herein.

The term "does not bind significantly" as applied to the novel monoclonal antibodies of the present invention means that the binding is not statistically significant as compared to controls wherein no binding occurs.

The term "chronic kinetics" as applied to the antigens defined by the novel monoclonal antibodies of the present invention means that the antigens continue to be expressed on human endothelial cells in the presence of IL-1 for a period of about 72 to 96 hours and that the expression is at levels above or about equal to the level initially reached upon addition of IL-1. Two examples of such behavior are shown in FIG. 7 for the antigens defined by monoclonal antibodies 1E7 and 2G7.

The term "acute kinetics" as applied to the antigens defined by the novel monoclonal antibodies of the present invention means that the antigens decrease and might disappear altogether from human endothelial cells in the presence of IL-1 within a period of about 24 hours from the initial addition of IL-1. One example of such behavior is shown in FIG. 7 for the antigen defined by monoclonal antibody 3A2.

The hybridomas according to the present invention can be produced reproducibly by routine experimentation according to established methods. The immunogen for preparing immunized cells is IL-1 activated human endothelial cells.

Human endothelial cells can be obtained from umbilical cords according to known methods (Jaffe, et al., J. Clin. Invest., 52:2745-2757, 1973). Briefly, cells are stripped from the blood vessel walls by treatment with collagenase and cultured in gelatin coated tissue culture flasks in M199 medium containing 20% low endotoxin fetal calf serum, 90 µg/ml preservative-free porcine heparin, 20 µg/ml endothelial cell growth supplement (ECGS), glutamine and antibodies. ECGS is a crude growth factor preparation obtained from bovine hypothalamus, the key ingredient being fibroblast growth factor. ECGS is commercially available.

The endothelial cells are activated by addition of IL-1 beta at 1 ng/ml for 4 hours. IL-1 beta is readily available to those skilled in the art, both commercially and otherwise.

The particular host being immunized for eventual production of hybridomas is not critical to the present invention, but should be a mouse. Balb/c mice are preferred.

The immunization schedule and amount of activated endothelial cells used for immunizing the mouse can readily be determined by the skilled artisan. By way of example, one suitable immunization schedule for Balb/c mice is to inject $3 \times 10^{-6}$ IL-1 activated human endothelial cells on 4 occasions, 10 days apart. the last injection being 3 to 4 days prior to fusion.

The sensitized cells, e.g., immunized spleen cells, are removed and splenocytes are fused with the SP2/0 myeloma cell line or other suitable myeloma cell line by well established techniques (Köhler. G. and Milstein, C. Nature. 256:495–497, 1975 and Young, W. W. et al, *J. Exp. Med.,* 150:1008–1019, 1979). Fusions are preferably carried out with polyethylene glycol.

The particular myeloma cells employed in the present invention for fusion with the sensitized spleen cells of the immunized host are not critical thereto and can be any well known myeloma cell useful for preparing hybridomas of mouse origin. Examples of such myeloma cells include HAT sensitive mice myeloma cells such as NS/1, SPI and SP2/0 cells.

The fused cells are cultured under conditions readily determined by the skilled artisan.

After an appropriate culture period, hybridoma, producing monoclonal antibodies that react with IL-1 activated endothelial cells but not with normal resting endothelial cells are cloned and subcloned by limiting dilution.

In general, screening is performed on confluent monolayers of resting or IL-1 activated endothelial cells. Culture supernatants are added to the monolayers of cells and incubated for a suitable period of time, e.g., 60 minutes at 4° C., to allow the monoclonal antibodies in the culture supernatants to react with the monolayers of cells. Antibody bound to an antigen-coated well is usually detected by secondary antibody, e.g., biotinylated anti-mouse IgM and IgG goat or rabbit antibodies, followed by a suitable radioactive probe. e.g., $^{125}$I-streptavidin.

Monoclonal antibodies produced by hybridomas thus isolated according to the present invention can be produced in quantity by growing large batches of hybridoma cell cultures and purifying the antibody from the supernatant or by injecting mice with the hybridoma line to stimulate the production of ascites fluid. Both methods are well known in the art.

According to the above-described method, four hybridomas that produce preferred monoclonal antibodies have been produced. The preferred monoclonal antibodies were designated 1E7, 2G7, 3A2 and 7A9. The hybridomas producing these monoclonal antibodies, designated hybridoma 1E7. 2G7. 3A2 and 7A9, have been deposited with the American Type Culture Collection, Rockville, Maryland, and have ATCC Deposit Nos. HB 10136, HB 10137, HB 10138, and HB 10135, respectively.

Monoclonal antibody 1E7 according to the present invention is produced by hybridoma 1E7 and has, at a minimum, the following identifying characteristics:
(1) binds to IL-1 activated human endothelial cells;
(2) does not bind significantly to normal resting human endothelial cells;
(3) does not bind significantly to normal resting or IL-1 activated human epidermal keratinocytes or resting or IL-1 activated human fibroblasts;
(4) does not bind significantly to normal resting or IL-1 activated human granuocytes or mononuclear cells (T-cells, B-cells and monocytes);
(5) does not block binding of a mixture of mononuclear cells comprising T-cells B-cells and NK cells to IL-1 activated human endothelial cells in vitro;
(6) distribution of antigen: IL-1 activated human endothelial cells;
(7) antigen size, as measured by SDS polyacrylamide gel electrophoresis under reducing conditions:
  (a) major band at about 125 Kd,
  (b) minor band at about 97 Kd;
(8) antigen size, as measured by SDS polyacrylamide gel electrophoresis under non-reducing conditions:
  (a) major band at about 99 Kd,
  (b) minor band at about 87 Kd; and
(9) exhibits chronic kinetics as determined by ability of the monoclonal antibody to bind to human endothelial cells pretreated for increasingly longer periods of time with IL-1.

Further monoclonal antibody 1E9 is a murine monoclonal antibody and its isotype is IgG2a.

Monoclonal antibody 2G7 according to the present invention is produced by hybridoma 2G7 and has, at a minimum, the following identifying characteristics:
(1) binds to IL-1 activated human endothelial cells;
(2) does not bind significantly to normal resting human endothelial cells;
(3) does not bind significantly to normal resting or IL-1 activated human epidermal keratinocytes or resting or IL-1 activated human fibroblasts;
(4) does not bind significantly to normal resting or IL-1 activated human granulocytes or mononuclear cells (T-cells, B-cells and monocytes);
(5) partially blocks binding of a mixture of cells comprising T-cells, B-cells and monocytes to IL-1 activated human endothelial cells in vitro;
(6) distribution of antigen: IL-1 activated endothelial cells;
(7) antigen size, as measured by SDS polyacrylamide gel electrophoresis under reducing conditions:
  (a) major band at about 125 Kd,
  (b) minor band at about 97 Kd;
(8) antigen size, as measured by SDS polyacrylamide gel electrophoresis under non-reducing conditions:
  (a) major band at about 99 Kd,
  (b) minor band at about 87 Kd; and
(9) antigen exhibits chronic kinetics as determined by ability of the monoclonal antibody to bind to human endothelial cells pretreated for increasingly longer periods of time with IL-1.

Further, monoclonal antibody 2G7 is a murine monoclonal antibody and its isotype is IgG1.

Monoclonal antibody 3A2 according to the present invention is produced by hybridoma 3A2 and has, at a minimum, the following identifying characteristics:
(1) binds to IL-1 activated human endothelial cells;
(2) does not bind significantly to normal resting human endothelial cells;
(3) does not bind significantly to normal resting or IL-1 activated human epidermal keratinocytes or resting or IL-1 activated human fibroblasts;
(4) does not bind significantly to normal resting or IL-1 activated human granulocytes or mononuclear cells (T-cells, B-cells and monocytes);
(5) distribution of antigen: IL-1 activated human endothelial cells;
(6) antigen size, as measured by SDS polyacrylamide gel electrophoresis under reducing and non-reducing conditions: 177 Kd; and
(7) antigen exhibits acute kinetics as determined by ability of the monoclonal antibody to bind to human endothelial cells pretreated for increasingly longer periods of time with IL-1.

Further, monoclonal antibody 3A2 is a murine monoclonal antibody and its isotype is IgM.

Monoclonal antibody 7A9 according to the present invention is produced by hybridoma 7A9 and has, at a minimum, the following identifying characteristics:
(1) binds to IL-1 activated human endothelial cells;
(2) does not bind significantly to normal resting human endothelial cells;
(3) does not bind significantly to normal resting or IL-1 activated human epidermal keratinocytes or resting or IL-1 activated human fibroblasts;
(4) does not bind significantly to normal resting or IL-1 activated human granulocytes or mononuclear cells (T-cells, B-cells and monocytes);
(5) blocks binding of granulocytes to IL-1 activated human endothelial cells in vitro;
(6) partially blocks binding of monocytes to IL-1 activated human endothelial cells in vitro;
(7) distribution of antigen: IL-1 activated human endothelial cells;
(8) antigen size, as measured by SDS polyacrylamide gel electrophoresis under reducing conditions: about 100 Kd; and
(9) antigen size, as measured by SDS polyacrylamide gel electrophoresis under non-reducing conditions: about 90 Kd.

Further monoclonal antibody 7A9 is a murine monoclonal antibody and its isotype is IgG1.

Novel Antigen

The present invention also provides a novel purified antigen or antigenic fragment thereof, the antigen having the following identifying characteristics.
(1) distribution: IL-1 activated human endothelial cells;
(2) size as measured by SDS polyacrylamide gel electrophoresis under reducing conditions: about 100 Kd;
(3) size as measured by SDS polyacrylamide gel electrophoresis under non-reducing conditions: 90 about Kd; and
(4) binds to monoclonal antibody 7A9 produced by hybridoma cell line 7A9 having ATCC Deposit No. HB 10135.

The novel antigen can be prepared and purified by conventional methods. For use in a soluble form, the antigen or antigenic fragment thereof, should be synthetically produced. The antigen can be cloned and sequenced according to known methods (see, for example, Bevilacqua, M. P. et al, *Science*, 243: 1160-1164, 1989). Determination of the active site or sites is also by standard techniques (see, for example, Peterson, A. and Seed, B. *Cell*, 54: 65-72, 1988) as is synthesis of the peptide fragments.

The novel antigen is useful in its soluble form to block the interaction of white blood cells with activated endothelial cells, as described in more detail below in the section entitled "Medicaments and Methods for Blocking Inflammatory Responses".

The novel antigen is also useful to assay for blocking binding of white blood cells to activated endothelial cells. The skilled artisan can readily determine suitable assay conditions.

Medicaments and Methods for Blocking Inflammatory Responses

The present invention also provides medicaments and methods for blocking inflammatory responses with activated endothelial cells.

In one embodiment, the medicament comprises:
(A) A pharmaceutically effective amount of an antibody binding site of a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells, B-cells and monocytes);
(5) partially blocks binding of a mixture of cells comprising T-cells, B-cells and monocytes to IL-1 activated endothelial cells in vitro;
(6) distribution of antigen: IL-1 activated endothelial cells;
(7) antigen size, as measured by SDS polyacrylamide gel electrophoresis under reducing conditions:
  (a) major band at about 125 Kd,
  (b) minor band at about 97 Kd;
(8) antigen size, as measured by SDS polyacrylamide gel electrophoresis under non-reducing conditions:
  (a) major band at about 99 Kd,
  (b) minor band at about 87 Kd; and
(9) antigen exhibits chronic kinetics as determined by ability of the monoclonal antibody to bind to endothelial cells pretreated for increasingly longer periods of time with IL-1; and
(B) a pharmaceutically acceptable carrier, diluent or excipient.

In a second embodiment, the medicament comprises:
(A) a pharmaceutically effective amount of an antibody binding site of a monoclonal antibody having the following identifying characteristics:
(1) binds to IL-1 activated endothelial cells;
(2) does not bind significantly to normal resting endothelial cells;
(3) does not bind significantly to normal resting or IL-1 activated epidermal keratinocytes or resting or IL-1 activated fibroblasts;
(4) does not bind significantly to normal resting or IL-1 activated granulocytes or mononuclear cells (T-cells, B-cells and monocytes);
(5) blocks binding of granulocytes to IL-1 activated endothelial cells in vitro;
(6) partially blocks binding of monocytes to IL-1 activated endothelial cells in vitro;
(7) distribution of antigen: IL-1 activated endothelial cells;
(8) antigen size, as measured by SDS polyacrylamide gel electrophoresis under reducing conditions: about 100 Kd; and
(9) antigen size, as measured by SDS polyacrylamide gel electrophoresis under non-reducing conditions: about 90 Kd; and
(B) a pharmaceutically acceptable carrier, diluent or excipient.

In a third embodiment, the medicament comprises:

(A) a pharmaceutically effective amount of a purified antigen or antigenic fragment thereof, the antigen having the following identifying characteristics:
   (1) distribution: IL-1 activated human endothelial cells;
   (2) size as measured by SDS polyacrylamide gel electrophoresis under reducing conditions: about 100 Kd;
   (3) size as measured by SDS polyacrylamide gel electrophoresis under non-reducing conditions: about 90 Kd; and
   (4) binds to monoclonal antibody 7A9 produced by hybridoma cell line 7A9 having ATCC Deposit No. HB 10135; and
(B) a pharmaceutically acceptable carrier, diluent or excipient.

Similarly, in one embodiment the method comprises treating a subject in need of treatment with a pharmaceutically effective amount of an antibody binding site of a monoclonal antibody having the following characteristics:
   (1) binds to IL-1 activated endothelial cells;
   (2) does not bind significantly to normal resting endothelial cells;
   (3) does not bind significantly to normal resting or IL-1 activated epidermal keratinocytes or resting or IL-1 activated fibroblasts;
   (4) does not bind significantly to normal resting or IL-1 activated granulocytes or mononuclear cells (T-cells, B-cells and monocytes);
   (5) partially blocks binding of a mixture of cells comprising T-cells, B-cells and monocytes to IL-1 actived endothelial cells in vitro;
   (6) distribution of antigen: IL-1 activated endothelial cells;
   (7) antigen size, as measured by SDS polyacrylamide gel electrophoresis under reducing conditions:
      (a) major band at about 125 Kd,
      (b) minor band at about 97 Kd;
   (8) antigen size, as measured by SDS polyacrylamide gel electrophoresis under non-reducing conditions:
      (a) major band at about 99 Kd,
      (b) minor band at about 87 Kd; and
   (9) antigen exhibits chronic kinetics as determined by ability of the monoclonal antibody to bind to endothelial cells pretreated for increasingly longer periods of time with IL-1.

In a second embodiment, the method comprises treating a subject in need of treatment with a pharmaceutically effective amount of an antibody binding site of a monoclonal antibody having the following identifying characteristics:
   (1) binds to IL-1 activated endothelial cells;
   (2) does not bind significantly to normal resting endothelial cells;
   (3) does not bind significantly to normal resting or IL-1 activated epidermal keratinocytes or resting or IL-1 activated fibroblasts;
   (4) does not bind significantly to normal resting or IL-1 activated granulocytes or mononuclear cells (T-cells, B-cells and monocytes);
   (5) blocks binding of granulocytes to IL-1 activated endothelial cells in vitro;
   (6) partially blocks binding of monocytes to IL-1 activated endothelial cells in vitro;
   (7) distribution of antigen: IL-1 activated endothelial cells;
   (8) antigen size, as measured by SDS polyacrylamide gel electrophoresis under reducing conditions: about 100 Kd; and
   (9) antigen size, as measured by SDS polyacrylamide gel electrophoresis under non-reducing conditions: about 90 Kd.

In a third embodiment the method comprises treating a subject in need of treatment with a pharmaceutically effective amount of a purified antigen or antigenic fragment thereof the antigen having the following identifying characteristics:
   (1) distribution: IL-1 activated human endothelial cells;
   (2) size as measured by SDS polyacrylamide gel electrophoresis under reducing conditions: about 100 Kd;
   (3) size as measured by SDS polyacrylamide gel electrophoresis under non-reducing conditions: 90 about Kd; and
   (4) binds to monoclonal antibody 7A9 produced by hybridoma cell line 7A9 having ATCC Deposit No. HB 10135.

The monoclonal antibodies useful as medicaments and in the methods of treatment are the same as those described above that are capable of blocking binding of white blood cells to IL-1 activated endothelial cells, and in preferred embodiments, the monoclonal antibodies are -2G7 and 7A9, described above. The antigen useful as a medicament and in the method of treatment is the same as the novel antigen described above.

Suitable pharmaceutically acceptable carriers, diluents or excipients can readily be determined by the skilled artisan.

The medicaments are administered intravenously.

Suitable doses to be administered might vary depending upon the nature of the inflammatory disorder, but can readily be determined by the skilled artisan.

In general, a suitable dose for intravenous injection to humans is about 20 to 50 mg of the monoclonal antibody binding site or antigen.

FIG. 1 is a simplified schematic representation of how the medicaments and methods of treatment according to the present invention are believed to work.

The medicaments and methods of treatment are applicable to any inflammatory response associated with activated endothelial cells, and can be used for acute as well as chronic inflammations.

Of course combinations of the various medicaments can always be used, as long as the novel antigen is not combined in one medicament with its corresponding monoclonal antibody.

One skilled in the art can readily determine the inflammatory responses for which the medicaments and methods of treatment of the present invention will be useful. Examples include tumor-cell-mediated vasular damage, rheumatoid arthritis, post-reperfusion myocardial injury (damage by granulocytes) and adult respiratory distress syndrome (macrophages and granulocytes). Examples are also disclosed in Simpson, P. J. et al. *J. Clin. Invest.*, 81: 624–629, 1988; Vedder. N. B. et al *J. Clin. Invest.*, 81: 939–944, 1988; Simon and Ward "Adult Respiratory Distress Syndrome" in *Inflammation: Basic Principles and Clinical Correlates* (Gallin. J. I., Goldstein, I. M. and Synderman, R.: eds) Raven Press, N.Y., 1988, page 815; Kadison and Barton "Vasculitis: Mechanisms of Vessel Damage" Id. page 703; and Harris "Pathogenesis of Rheumatoid Arthritis: A Disorder Associated with Dysfunctional Immunoregulation" Id. page 751.

Method of Detecting Inflammatory Responses

The present invention also provides a method for detecting inflammatory responses associated with activated endothelial cells the method comprising:
(I) contacting a blood sample with an antibody selected from the group consisting of:
  (A) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells, B-cells, and monocytes);
    (5) does not block binding of a mixture of mononuclear cells comprising T-cells, B-cells and NK cells to IL-1 activated endothelial cells in vitro;
    (6) distribution of antigen: IL-1 activated endothelial cells;
    (7) antigen size, as measured by SDS polyacrylamide gel electrophoresis under reducing conditions:
      (a) major band at about 125 Kd,
      (b) minor band at about 97 Kd;
    (8) antigen size, as measured by SDS polyacrylamide gel electrophoresis under non-reducing conditions:
      (a) major band at about 99 Kd,
      (b) minor band at about 87 Kd; and
    (9) exhibits chronic kinetics as determined by ability of the monoclonal antibody to bind to endothelial cells pretreated for increasingly longer periods of time with IL-1;
  (B) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activate fibroblasts;
    (4) does not bind significantly to normal resting or IL-1 activated granulocytes or mononuclear cells (T-cells, B-cells and monocytes);
    (5) partially blocks binding of a mixture of cells comprising T-cells, B-cells and monocytes to IL-1 activated endothelial cells in vitro;
    (6) distribution of antigen: IL-1 activated endothelial cells;
    (7) antigen size, as measured by SDS polyacrylamide gel electrophoresis under reducing conditions:
      (a) major band at about 125 Kd,
      (b) minor band at about 97 Kd;
    (8) antigen size, as measured by SDS polyacrylamide gel electrophoresis under non-reducing conditions:
      (a) major band at about 99 Kd,
      (b) minor band at about 87 Kd; and
    (9) antigen exhibits chronic kinetics as determined by ability of the monoclonal antibody to bind to endothelial cells pretreated for increasingly longer periods of time with IL-1;
  (C) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells, B-cells, and monocytes);
    (5) distribution of antigen: IL-1 activated endothelial cells;
    (6) antigen size, as measured by SDS polyacrylamide gel electrophoresis under reducing and non-reducing conditions: about 177 Kd; and
    (7) antigen exhibits acute kinetics as determined by ability of the monoclonal antibody to bind to endothelial cells pretreated for increasingly longer periods of time with IL-1; and
  (D) a monoclonal antibody having the following identifying characteristics:
    (1) binds to IL-1 activated endothelial cells;
    (2) does not bind significantly to normal resting endothelial cells;
    (3) does not bind significantly to normal resting or IL-1 activated epidermal keratinocytes or resting or IL-1 activated fibroblasts;
    (4) does not bind significantly to normal resting or IL-1 activated granulocytes or mononuclear cells (T-cells, B-cells and monocytes);
    (5) blocks binding of granulocytes to IL-1 activated endothelial cells in vitro;
    (6) partially blocks binding of monocytes to IL-1 activated endothelial cells in vitro;
    (7) distribution of antigen: IL-1 activated endothelial cells;
    (8) antigen size, as measured by SDS polyacrylamide gel electrophoresis under reducing conditions: about 100 Kd; and
    (9) antigen size, as measured by SDS polyacrylamide gel electrophoresis under non-reducing conditions: about 90 Kd: and
(II) assaying for specific binding of said antibody to antigen in said test sample.

In a preferred embodiment, the method comprises:
(I) contacting a blood sample with an antibody selected from the group consisting of:
  (A) a monoclonal having the identifying characteristics of monoclonal antibody 1E7 produced by hybridoma 1E7 having ATCC Deposit No. HB 10136;
  (B) a monoclonal having the identifying characteristics of monoclonal antibody 2G7 produced by hybridoma 2G7 having ATCC Deposit No. HB 10137;
  (C) a monoclonal having the identifying characteristics of monoclonal antibody 3A2 produced by hybridoma 3A2 having ATCC Deposit No. HB 10138;
  (D) a monoclonal having the identifying characteristics of monoclonal antibody 7A9 produced by hybridoma 7A9 having ATCC Deposit No. HB 10135; and
(II) Assaying for specific binding of said antibody to antigen in said test sample.

The method of producing and purifying the monoclonal antibodies has already been described above.

Detection can occur either in vitro or in vivo. In vitro detection can be carried out using any of the well known in vitro immunological assays, such as those described by Young, W. W. et al, *J. Exp. Med.*, 150: 1008–1019 (1979) and Kannagi, R. et al *Cancer Res.*, 43: 4997–5005 (1983). Further, in vivo, detection can be carried out using any of the well known in vivo immunological assays such as those described in Burchell J. et al, *Int. J. Cancer* 34: 763–768 (1984); Epenetos, A. A. et al, *Lancet.* 2: 999–1004 (1982): Chatal, J.-F. et al, *J. Nuclear Med.*, 26: 531–537 (1985)..

The method can be used, for example, to detect early graft rejection or subclinical infections or vasculitis.

EXAMPLES

The present invention will now be described by reference to specific examples, which are not meant to be limiting.

Unless otherwise specified all percents, ratios, parts, etc. are by volume.

The reagents used in the Examples were obtained and/or treated as follows: Triton X-100, porcine intestinal heparin, collagenase type 1 were purchased from Sigma. Tween 20 was purchased from Aldrich. Gelatin was purchased from Bio Rad. Biotinylated goat anti-mouse reagent and FITC-goat anti-mouse reagent were purchased from Jackson Immunoresearch, Affinity purified goat anti-mouse IgG was purchased from Kirkegaard and Perry Labs, and $^{125}$I-streptavidin was purchased from Amersham. Recombinant human IL-1 beta was a gift from Dr. Y Hirai of the Tokushima Research Institute. The material was purified from *E. coli* and gave a single band at 17 Kd on acrylamide gel electrophoresis.

EXAMPLE 1

Preparation of Monoclonal Antibodies Specific to Activated Human Endothelial Cells Cell Culture Discarded umbilical cords, obtained with permission of the hospital review board, were processed according to the procedure of Jaffe (*J., Clin. Invest.*, 52:2745–2757, 1973) with minor modifications to obtain human umbilical vein endothelial cells (HUVE). Briefly, cells were stripped from the blood vessel walls by treatment with collagenase and cultured in gelatin coated tissue culture flasks in the medium described below. Cells were determined to be greater than 95% endothelial by virtue of the presence of Weibel-Palade bodies and uptake of acetyleted low density lipoprotein by viable cells. Cells were cultured in M199 medium containing 20% low endotoxin fetal calf serum (FCS). 90 ug/ml preservative-free porcine heparin, 20 ug/ml endothelial cell growth supplement (EFGS) (from collaborative Research), glutamine and antibiotics (hereinafter "growth medium").

Hybridoma Production

Female Balb/c mice at 8 weeks of age were injected intraperitoneally with $3 \times 10^6$ IL-1 (4 h) activated HUVE on 4 occasions, 10 days apart, the last injection being 3 to 4 days prior to fusion. Spleens were aseptically removed, minced with a syringe plunger, washed and mixed with the SP2/0 fusion partner (Fazekas de St. Groth, S. and Scheidegger, D., *J. Immunol Methods* 35: 1–21, 1980) in a ratio of five to 1. The cells were fused with polyethylene glycol as previously described (Kohler, G. and Milstein, C., *Nature*, 256: 495–497, 1975) and plated into 6 to 8 96 well miocrotiter plates containing resident peritoneal exudate cells from Balb/c mice. Screening was performed on confluent monolayers of resting or IL-1 activated HUVE (activated by addition of IL-1 at 1 ng/ml for 4 hrs) also in 96 well plates. After allowing 60 minutes at 4° C. for the culture supernatants to react with the monolayers of HUVE. cells were washed and incubated with biotinylated goat anti-mouse antibody for 30 minutes at 4° C. After 3 more rinses, cells were incubated for 15 minutes at 4° C. with $^{125}$I-streptavidin. After final rinses, cells were lysed with 1% Triton X-100 detergent solution, and aliquots counted in a gamma counter. Hybridomas were selected based upon their ability to secrete antibodies which reacted exclusively with IL-1 treated but not with untreated HUVE, According to this method, four hybridoma cell lines were obtained that produced the desired monoclonal antibodies. These hybridoma cell lines and the monoclonal antibodies they produced were designated 1E7. 2G7, 3A2 and 7A9. The hybridomas have been deposited with the American Type Culture Collection in Rockville. Maryland and have Deposit Nos. HB 10136, HB 10137, HB 10138, and HB 10135, respectively.

EXAMPLE 2

Characterization of Monoclonal Antibodies 1E7, 2G7, 3A2 and 7A9

Isotype Determination

Isotype was determined by using "ScreenType", a kit containing all of the necessary reagents, from Boehringer-Mannheim, Indianapolis, Ind. The isotype determination was performed according to the manufacturer's instructions.

The results, which are summarized in Table I. were as follows: 1E7—IgG2a: 2G7—IgG1; 3A2—IgM; and 7A9—IgG1.

Blocking Activity

Endothelial cells were obtained from discarded umbilical cords and cultured as described in Example 1. Cells multiplied rapidly and were subdivided (passaged) up to 6 times into other flasks before their differentiated properties declined, perhaps as a result of the in vitro growth conditions. By the second passage sufficient cells were available to perform blocking assays. Recombinant human IL-1 beta was added at a concentration of 1 ng/ml to cells in culture for 4 to 6 hours while the cells were maintained as usual in a humidified incubation chamber containing 6% $CO_2$, 94% air. Controls consisted of culturing endothelial cells in the absence of IL-1. After the incubation period, cells were rinsed with medium to remove unused IL-1, and the respective monoclonal antibodies were added at concentrations ranging from 0.0016 to 10 µg/ml for 1 h at 37° C. The F(ab')$_2$ fragment of monoclonal antibody 2G7, obtained by conventional methods, was also used for this assay. After the incubation period, cells were rinsed with medium to remove excess monoclonal antibody and the cells whose binding was being studied were overlaid for 30 to 60 minutes to allow attachment. The cells used were human monocytes, granulocytes or a mixture of mononuclear cells comprising T-cells, B-cells and NK cells. These cells were isolated and purified by methods known in the art. The non-adherent cells were washed off by rinsing with growth medium, and the difference in the number of cells bound to endothelial cells(EC) untreated or treated with IL-1 was observed.

This assay was performed in a quantitative manner by incorporating a radioactive tracer. e.g., $^{51}$Cr, by methods known in the art, into the cytoplasm of the cells whose binding was being studied, washing to remove any extracellular counts, and placing these labeled cells over the EC monolayer. The $^{51}$Cr label used for this purpose showed minimal leakage during the 30 to 60 minutes of the binding assay. After rinsing to remove non-adherent cells, the monolayers were solubilized with detergent. The radioactivity counted from each well was a measure of the numbers of cells bound.

The results showing inhibition of mononuclear cell binding by the F(ab')$_2$ fragment of monoclonal antibody 2G7 and of monoclonal antibody 1E7 are shown in FIG. 2. The results show that monoclonal antibody 2G7, but not monoclonal antibody 1E7, when used to pretreat IL-1 activated endothelial cells, causes dose-dependent partial inhibition of the binding of human mononuclear cells to endothethial cells. The F(ab')$_2$ fragment of monoclonal antibody 7A9 also showed dose-dependent inhibition of cells as shown in Table I.

The results for all four monoclonal antibodies are summarized in Table I.

let monoclonal antibody (Hsu-Lin et al, *J. Biol. Chem.*, 259: 9121–9126, 1984). Of published monoclonal antibodies, KC4 has the closest specificity to that of monoclonal antibody 3A2 of the present invention. However monoclonal antibody KC4 has an isotype of IgG1 whereas monoclonal antibody 3A2 has the unexpected isotype of IgM. 4D10 is a rat monoclonal antibody having specificity for IL-1 stimulated endothelial cells (Goerdt et al *Expl. Cell Biol.*, 55: 117–126, 1987). Monoclonal antibody 4D10 has no obvious relation to the antibodies of the present invention. However, the antigen to which monoclonal antibody 4D10 binds is closest in molecular weight to the antigen to which monoclonal antibody 7A9 binds.

The comparisons in Table I demonstrate that the monoclonal antibodies according to the present invention have unexpected properties over the closest published monoclonal antibodies.

EXAMPLE 3

Characterization of Specificity of Monoclonal Antibodies of Present Invention with Published Antibodies Antigen Size Confluent cultures of low passage (less than p6) human umbilical vein endothelial cells (HUVE) in 100

TABLE I

Comparison of Monoclonal Antibodies of Present Invention With Published Antibodies

| Name | Origin or Ref. | Isotype | Species | Blocking Activity | Immunogen* | Reference |
|---|---|---|---|---|---|---|
| H4/18 | Prober et al | IgG1 | Mouse | None | IL-1-EC | J. Immunol, 136:1680 (1986) |
| H18/7 | Bevilacqua et al | IgG2a | Mouse | Partial Granulocytes | TNF-EC | P.N.A.S. 84:9238 (1987) |
| 1E7 | Invention | IgG2a | Mouse | None | IL-1-EC | |
| 2G7 | Invention | IgG1 | Mouse | Partial Perhaps T or B Cells or Granulocytes | | |
| S12 | McEver et al | IgG1 | Mouse | Not Done | Platelets | J. Biol. Chem. 259:9799 (1984) |
| KC4 | Hsu-Lin et al | IgG1 | Mouse | Not Done | Platelets | J. Biol. Chem. 259:9121 (1984) |
| 3A2 | Invention | IgM | Mouse | Not Done | IL-1-EC | |
| 4D10 | Goerdt et al | IgG2a | Rat | None | lps 24h | Exp. Cell. Biol. 55:117 (1987) |
| 7A9 | Invention | IgG1 | Mouse | Granulocytes Total, Monocytes Partial | IL-1-EC | |

*Abbreviations are as follows:
IL-1-EC (interleukin-1 activated endothelial cells);
TNF-EC (tumor necrosis factor activated endothelial cells);
lps 24h (24h endotoxin (lipopolysaccharide, LPS) activated endothelial cells).

Table I compares properties of the monoclonal antibodies according to the present invention with those of the closest published antibodies. H4/18 is the first antibody raised against IL-1 stimulated endothelial cells (Pober. et al. *J. Immunol* 136:1680–1687, 1986). H18/7 is a monoclonal antibody raised against IL-1 stimulated endothelial cells and it partially blocks granulocyte adhesion to IL-1 stimulated endothelial cells (Bevilacqua et al, *Proc. Natl. Acad. Sci.*, 84: 9238–9241, 1987). S12 is a monoclonal antibody that binds to activated platelets and is most closely compared to monoclonal antibody 3A2 of the present invention (McEver and Martin, *J. Biol. Chem.*, 259:9799–9804, 1984). Unexpectedly, however, monoclonal antibody 3A2 has an IgM isotype while that of S12 is IgG1. The IgM isotype is unusual for a monoclonal antibody KC4 is an antiplatemm tissue culture dishes were placed overnight in a low methionine containing medium. The next day, IL-1 was added to 1 ng/ml and $^{35}$S-methionine (Amersham) was added in the ratio of 250 $\mu$Ci/10$^7$ cells. IL-1 was not added to controls. After 6 h of culture at 37° C., the monolayers were rinsed three times with ice cold Dulbecco's phosphate buffered saline (D-PBS) and lysed with 250 $\mu$l of a 1% solution of Triton X-100 lysing buffer.

Nunc ELISA 96-well microtiter plates were incubated with 25 $\mu$g of affinity purified goat anti-mouse antibody in 100 $\mu$l of 0.05M carbonate buffer, pH 9.5 for 1 h at room temperature. Wells were rinsed ten times with PBS-0.05% Tween 20, followed by addition of 100 $\mu$l of 1% BSA for1 h at room temperature. To each well, in the presence of BSA, was added 5 $\mu$g of purified monoclonal antibody for an additional 1 hour at room temperature. Following ten washes with PBS-Tween, 1–3×10⁶ cpm of lysate was added to each well cell types were human fibroblasts (MRHF) keratinocytes (NHEK) and endothelial cells (HUVEC).

The results are shown in Table II below.

TABLE II

| ANTIGEN DISTRIBUTION OF MAbs 1E7, 2G7, 3A2 & 7A9 USING HUVEC, NHEK AND MRHF | | | | | |
|---|---|---|---|---|---|
| | 1E7 | 2G7 | 3A2 | 7A9 | No MAb |
| Cells + IL-1 | | | | | |
| HUVEC | 40,140 ± 769 | 16,389 ± 1888 | 6,425 ± 343 | 15,891 ± 362 | 439 ± 86 |
| NHEK | 1,042 ± 72 | 768 ± 25 | 1,570 ± 106 | 578 ± 20 | 627 ± 21 |
| MRHF | 1,189 ± 309 | 511 ± 28 | 638 ± 92 | 513 ± 38 | 391 ± 27 |
| Cells − IL-1 | | | | | |
| HUVEC | 1,934 ± 60 | 1,565 ± 130 | 806 ± 179 | 1,814 ± 47 | 293 ± 63 |
| NHEK | 959 ± 51 | 696 ± 53 | 1,651 ± 191 | 676 ± 26 | 647 ± 50 |
| MRHF | 863 ± 60 | 521 ± 60 | 608 ± 69 | 448 ± 29 | 495 ± 73 | at 4° C. for 2 h with gentle rocking. Wells were washed with PBS-Tween dried and extracted with reducing sample buffer and applied to SDS-polyacrylamide (SDS-PAGE) gells, either reducing or non-reducing The gels were 8% acrylamide for the 3A2 and 7A9 samples and 10% acrylamide for the 1E7 and 2G7 samples.

Figure 3:
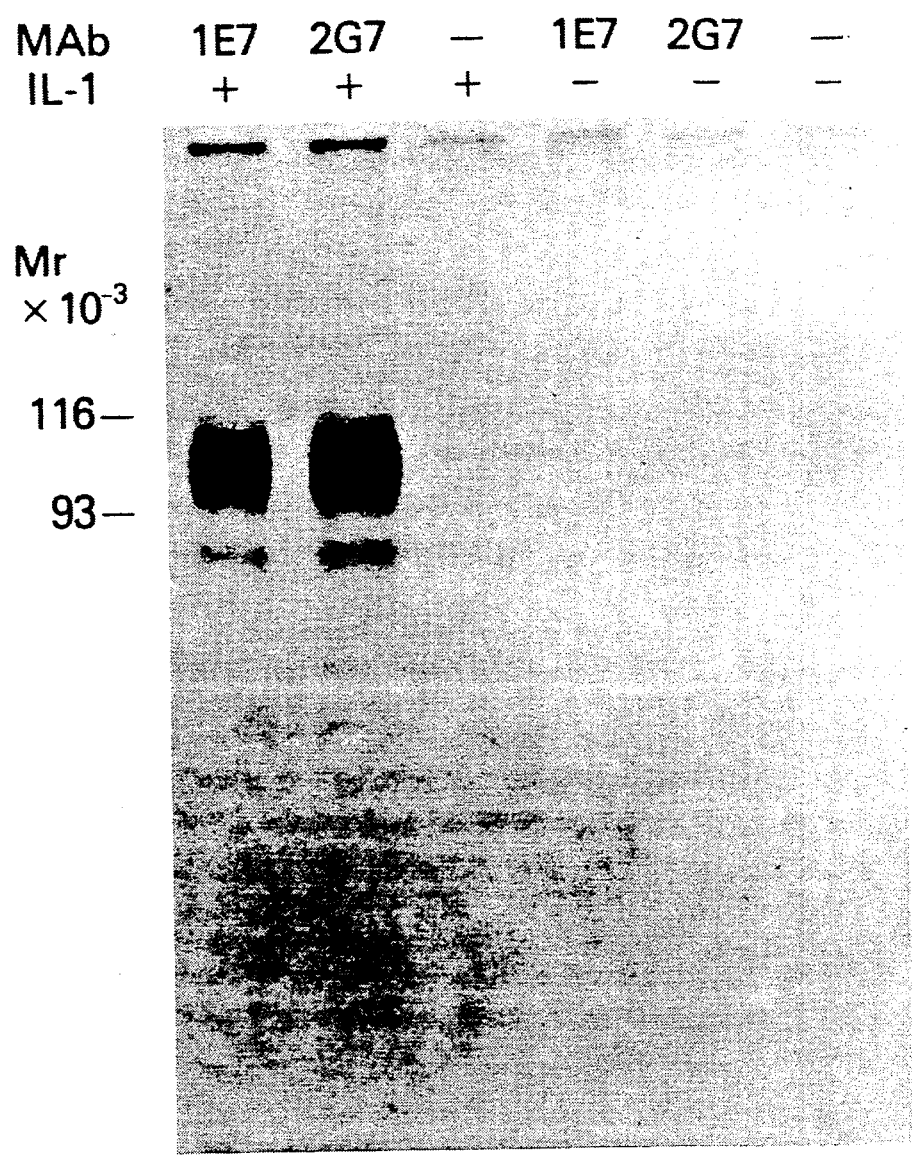
FIG. 3 is an SDS-PAGE pattern (10% acrylamide) of the antigens defined by the monoclonal antibodies 1E7 and 2G7 of the present invention under non-reducing conditions. Molecular weight standards are also shown.

The results are shown in FIGS. 3 and 4 and are summarized in Table III. The results were as follows:

(1) monoclonal antibody 1E7 and monoclonal antibody 2G7 lysates showed a major band at 125 Kd and a minor band at 97 Kd under reducing conditions and a major band at 99 Kd and a minor band at 87 Kd under non-reducing conditions; (results under reducing conditions are not shown in the figures);

(2) monoclonal antibody 3A2 lysates showed one band at 177 Kd under reducing and non-reducing conditions, and;

(3) monoclonal antibody 7A9 lysates showed one band at 100 Kd under reducing conditions and one band at 90 Kd under non-reducing conditions.

Antigen Distribution

General binding assay

For this assay 20,000 human umbilical vein endothelial (HUVE) cells were plated in each well of a 96 well microtiter plate on a gelatin coated surface. Cells were left overnight in growth medium (See Example 1) to allow full attachment. The following day cells were exposed to 1 ng/ml IL-1 for 4 h, washed and incubated separately with each of the monoclonal antibodies at 5 μg/ml. Controls consisted of HUVE not exposed to IL-1, or exposed to IL-1 but not exposed to antibody After 1 h incubation at 4° C., cells were washed and incubated with biotinylated goat anti-mouse reagent at a 1/1000 dilution. After 30 minutes at 4° C., cells were rinsed and exposed to a 1/10 dilution of ¹²⁵I-Streptavidin. After 15 minutes at 4° C., cells were rinsed and lysed with Triton X100 detergent (1%, and aliquots were counted in a gamma counter.

The results are shown in FIG. 5. FIG. 5 shows that all four monoclonal antibodies, 1E7, 3A2, 7A9 and 2G7 bind to IL-1 activated human endothelial cells (HEC), but not significantly to normal resting HEC. This indicates that the antigens to which monoclonal antibodies 1E7, 3A2. 7A9 and 2G7 bind are found on IL-1 activated HEC.

The presence of the antigen corresponding to each of the four monoclonal antibodies was determined as in the general binding assay except that in addition to endothelial cells other cell types were used and the incubation time (as above) with IL-1 was for 4 h. The other The data in Table II show that all four monoclonal antibodies, 1E7,3A2. 7A9 and 2G7 bind to IL-1 activated HEC, but not significantly to normal resting or IL-1 activated human epidermal keratinocytes or resting or IL-1 activated human fibroblasts. This data indicates that the antigens to which monoclonal antibodies 1E7, 3A2, 7A9 and 2G7 bind are found on IL-1 activated HEC.

The same protocol as for the general binding assay was used except that instead of using endothelial cells, granulocytes and mononuclear cells (T-. B- and monocyte cells) were used. Granulocytes and mononuclear cells were isolated from human heparinized blood by Ficoll-Hypaque separation according to known methods.

The results are shown in FIG. 6. FIG. 6 shows that the four monoclonal antibodies 1E7. 3A2, 7A9 and 2G7 do not bind significantly to normal resting or IL-1 activated human granulocytes or mononuclear cells.

This data along with that from FIG. 5 and Table II indicate that the monoclonal antibodies 1E7, 3A2, 7A9 and 2G7 are specific for IL-1 activated HEC.

Antigen Kinetics

Endothelial cells (HUVE) were plated in different petri dishes (35 mm diameter) after gelatin coating of the plastic. Growth medium (described in Example 1) was added and the cells were cultured for the duration of the experiment in growth medium to which was added 1 ng/ml of IL-1. The times at which the cells were initially plated were staggered such that all cells were harvested on the same day but after different times of addition of IL-1 so that some cells were exposed to IL-1 for the last 12 h only, the full 96 h, or for intermediate times. The HUVE cells were detached from petri dishes using PBS/EDTA, washed twice in PBS-BSA and placed at 75.000 cells per well in round bottom microtiter plates. To these wells were added individually each of the four monoclonal antibodies at 5 μg/ml for 30 minutes at 4° C. After washing three times the cells were exposed to FITC-goat anti-mouse reagent at 1/40 dilution for 30 minutes at 4° C. After washing three additional times, the cells were examined for the degree of fluorescence on a Coulter model 541 EPICS flow cytometer according to established and routine procedures provided by the manufacturer. The results are shown in FIG. 7 and are expressed as the % positive (cells) vs the length of exposure to IL-1.

The data in FIG. 7 show that the antigens defined by monoclonal antibodies 1E7 and 2G7 increase in the presence of IL-1 and continue to be expressed in the presence of IL-1. In contrast, the antigen defined by monoclonal antibody 3A2 disappears with time. No zero time point is shown in this figure, the first time point is 4 h, by which point the 4 antigens are maximally exhibited.

Behavior such as that shown by the antigens defined by monoclonal antibodies 1E7 and 2G7 was designated as "chronic kinetics" to suggest that these antigens might be associated with chronic inflammation. Transient expression was designated as "acute kinetics" to suggest that these antigens might be associated with acute inflammation.

The data from Example 3 constitute additional identifying characteristics of the monoclonal antibodies of the present invention and of the novel antigen according to the present invention. The data are summarized in Table III and compared with similar data for the closest known published monoclonal antibodies.

TABLE III

COMPARISON OF SPECIFICITY OF MONOCLONAL ANTIBODIES OF PRESENT INVENTION WITH PUBLISHED ANTIBODIES

| Name | Ag Size (Kd)[1] Reducing | Non-Reducing | Ag Distribution[2] | Ag Kinetics | Remarks |
|---|---|---|---|---|---|
| 1E7 | 125, 97 | 99, 87 | IL-1-EC | Chronic | Invention |
| 2G7 | 125, 97 | 99, 87 | IL-1-EC | Chronic | Invention |
| 3A2 | 177 | 177 | IL-1-EC | Acute | Invention |
| 7A9 | 100 | 90 | IL-1-EC | Chronic | Invention |
| H4/18; H18/7 | 115, 97[3] | nd | IL-1-EC[4] | Acute[5] | Published |
| 4D10 | unknown | 81[6] | IL-1-EC[7] | Acute[8] | Published |
| S12 | 148[9] | 138[10] | Platelets, EC[11] | unknown | Published |

[1]Underline signifies major band.
[2]Abbreviations are as follows: IL-1-EC (interleukin-1 activated endothelial cells; EC (resting endothelial cells)
[3]Taken from Bevilacqua, Proc. Natl. Acad. Sci., 84:9238–9242, 1987.
[4]Taken from Bevilacqua, Proc. Natl. Acad. Sci., 94:9238–9242, 1987.
[5]Taken from Pober et al, J. Immunol., 136:1680–1687, 1986 and taken from Bevilacqua, Proc. Natl. Acad. Sci., 84:9238–9242, 1987.
[6]Taken from Goerdt, et al, Expl. Cell Biol. 55:117–126, 1987.
[7]Taken from Goerdt, et al, Expl. Cell Biol. 55:117–126, 1987.
[8]Taken from Goerdt, et al, Expl. Cell Biol. 55:117–126, 1987.
[9]Taken from McEver and Martin, J. Biol. Chem., 259:9799–9804, 1984.
[10]Taken from McEver and Martin, J. Biol. Chem., 259:9799–9804, 1984.
[11]Taken from McEver and Martin, J. Biol. Chem., 259:9799–9804, 1984.

The data in Table III demonstrate that the monoclonal antibodies according to the present invention are unexpectedly different from the closest known published monoclonal antibodies.

While the invention has been described in detail and with reference to specific examples thereof, it will be apparent to one skilled in the art that various changes and modifications can be made therein without departing from the spirit and scope thereof.

STATEMENT OF DEPOSIT

Hybridomas 1E7, 2G7, 3A2 and 7A9 were deposited with the American Type Culture Collection, 12301 Parklawn Drive, Rockville, Md. 20852, under the terms of the Budapest Treaty on the International Recognition of the Deposit of Microorganisms for the Purposes of Patent Procedure on May 9. 1989 and have ATCC deposit nos HB 10136, HB 10137, HB 10138 and HB 10135 respectively. All restrictions to access will be irrevocably removed upon grant of a United States patent on the instant application.

What is claimed is:

1. A hybridoma having all the identifying characteristics of hybridoma cell line 7A9 having ATCC Deposit No. HB 10135.

2. The hybridoma of claim 1, which is hybridoma cell line 7A9 having ATCC Deposit No. HB 10135.

3. A monoclonal antibody having all the identifying characteristics of monoclonal antibody 7A9 produced by hybridoma 7A9 having ATCC Deposit No. HB 10135.

4. The monoclonal antibody of claim 3, which is monoclonal antibody 7A9 produced by hybridoma 7A9 having ATCC Deposit No. HB 10135.

5. A medicament for blocking inflammatory responses associated with activated endothelial cells, the medicament comprising:
   (A) a pharmaceutically effective amount of a monoclonal antibody having all the identifying characteristics of monoclonal antibody 7A9 produced by hybridoma 7A9 having ATCC Deposit No. HB 10135; and
   (B) a pharmaceutically acceptable carrier, diluent or excipient.

6. The medicament of claim 5, wherein the monoclonal antibody is monoclonal antibody 7A9 produced by hybridoma 7A9 having ATCC Deposit No. HB 10135.

* * * * *